(12) United States Patent
Hall

(10) Patent No.: US 9,079,806 B2
(45) Date of Patent: Jul. 14, 2015

(54) ECO-PLANT AID

(71) Applicant: Kenneth W. Hall, Sarasota, FL (US)

(72) Inventor: Kenneth W. Hall, Sarasota, FL (US)

( * ) Notice: Subject to any disclaimer, the term of this patent is extended or adjusted under 35 U.S.C. 154(b) by 67 days.

(21) Appl. No.: 13/756,711

(22) Filed: Feb. 1, 2013

(65) Prior Publication Data

US 2014/0221204 A1    Aug. 7, 2014

(51) Int. Cl.
| | |
|---|---|
| *C05G 3/02* | (2006.01) |
| *C05F 11/00* | (2006.01) |
| *A01N 37/36* | (2006.01) |
| *A01N 41/04* | (2006.01) |
| *A01N 59/04* | (2006.01) |
| *A01N 59/14* | (2006.01) |

(52) U.S. Cl.
CPC *C05G 3/02* (2013.01); *A01N 37/36* (2013.01); *A01N 41/04* (2013.01); *A01N 59/04* (2013.01); *A01N 59/14* (2013.01); *C05F 11/00* (2013.01)

(58) Field of Classification Search
CPC ....... A01N 25/12; A01N 41/04; A01N 59/04; A01N 59/14; C05F 11/00; C05G 3/02
USPC .................................................. 504/101, 116
See application file for complete search history.

(56) References Cited

U.S. PATENT DOCUMENTS 5,424,270 A * 6/1995 Winston .................. 504/101
5,547,918 A * 8/1996 Newton et al. ............. 504/361

OTHER PUBLICATIONS

NPIC, Titled: Boric acid, the technical fact sheet, published May 2012.*

* cited by examiner

*Primary Examiner* — Ali Soroush
*Assistant Examiner* — Yanzhi Zhang
(74) *Attorney, Agent, or Firm* — Patent CEO; Phillip Vales

(57) ABSTRACT

A composition of matter having a powderized, tablet or dissolved in water solution having the following component compounds: Sodium Bicarbonate, Citric Acid, Sodium Lauryl Sulfonate, Polyethylene Glycol, Alkylbenzene Sulfonate, Boric Acid. The composition has several embodiments indicating various ranges for the compounds therein. Once liquefied the solution can be sprayed unto affected trees in order to provide nutritional benefits that may fight fungi, bacteria and viral pathogens that threaten the well being of plants as well as providing growth enhancing effects.

11 Claims, No Drawings

ECO-PLANT AID

FIELD OF THE INVENTION

The present invention relates to a composition presented in powder form or as a concentrated agricultural plant spray or liquid mixture. More particularly the invention provides a treatment for plants that has a fungicidal, nutritional, insecticidal and bacteriological treatment in a single application of the composition.

BACKGROUND OF THE INVENTION

The outside environment subjects plants to various stresses with which they are compelled to overcome. Chief amongst these are a large number of a disease causing catalysts such as viruses, pathogens, bacteria and fungi; additionally, insects can cause considerable damage to the plant in various ways such as the consumption of the leaves, trunk and more as well as assisting in the transmission of the aforementioned disease catalysts into the plant.

Citrus plants as well as other fruit bearing tress are the object of various disease causing catalysts that can also be spread therein by wind, rain and by other means. Various bacteria cause diseases such as the Canker and Greening disease with no known cure. The diseases have spread globally and local governments have even decided to destroy the affected trees as soon as the problem is detected. A bacterium is causing the citrus canker in Asia and the one causing the Greening Disease is vectored by an Asian insect known commonly as a citrus psyllid. These two, the Canker and Greening are particularly problematic for citrus crops as is the insect facilitating the disease.

Thus, these diseases have harmed untold numbers of farmsteads throughout the worlds and no known cure has been developed. Additionally, treatments have been developed that attempt to overcome the effects of the diseases but results have provided mixed results. For example, the response to the Canker in America consists primarily of the use of copper-based compounds to counteract the disease. These copper sprays have resulted in marginal benefits at best and require multiple reapplications that do not appear to be providing any benefits. Additionally, the mixtures employed do not provide sufficient nutritional benefits that can boost the health of plants and trees affected by one or more diseases.

Thus, there needs be a solution that overcomes these deficiencies and that is easy to use and made from common components that are inexpensive. Additionally, it is desirable to have a general composition that is powdered, water soluble and that can provide plant life with a nutritional supplement to overcome various adverse environmental factors.

SUMMARY OF THE INVENTION

A composition that provides plant nutritional assistance comprising:
Sodium Bicarbonate and
Citric Acid having a ratio of 40:22 citric acid to sodium bicarbonate.
In another aspect the composition further comprising:
Sodium Lauryl Sulfonate having a ratio of 20:22 of Sodium Lauryl Sulfonate to Sodium Bicarbonate and a ratio of 20:40 of Sodium Lauryl Sulfonate to citric acid.
In another aspect the composition further comprising:
Polyethylene Glycol having a ratio of 10:22 of Polyethylene Glycol to Sodium Bicarbonate and a ratio of 10:40 of Polyethylene Glycol to citric acid.
In another aspect the composition further comprising:
Alkylbenzene Sulfonate having a ratio of 5:22 of Alkylbenzene Sulfonate to Sodium Bicarbonate and a ratio of 5:40 of Alkylbenzene Sulfonate to citric acid.
In another aspect the composition further comprising:
Boric Acid having a ratio of 3:22 of Boric Acid to Sodium Bicarbonate and a ratio of 3:40 of-Boric Acid to citric acid.
In another aspect the composition further comprising:
Sodium Lauryl Sulfonate having a ratio of 20:22 of Sodium Lauryl Sulfonate to Sodium Bicarbonate and a ratio of 20:40 of Sodium Lauryl Sulfonate to citric acid and
Polyethylene Glycol having a ratio of 10:22 of Polyethylene Glycol to Sodium Bicarbonate and a ratio of 10:40 of Polyethylene Glycol to citric acid.
In another aspect the composition further comprising:
Alkylbenzene Sulfonate having a ratio of 5:22 of Alkylbenzene Sulfonate to Sodium Bicarbonate and a ratio of 5:40 of Alkylbenzene Sulfonate to citric acid and
Boric Acid having a ratio of 3:22 of Boric Acid to Sodium Bicarbonate and a ratio of 3:40 of-Boric Acid to citric acid.
In another aspect the composition further comprising:
Sodium Lauryl Sulfonate having a ratio of 20:22 of Sodium Lauryl Sulfonate to Sodium Bicarbonate and a ratio of 20:40 of Sodium Lauryl Sulfonate to citric acid
Polyethylene Glycol having a ratio of 10:22 of Polyethylene Glycol to Sodium Bicarbonate and a ratio of 10:40 of Polyethylene Glycol to citric acid
Alkylbenzene Sulfonate having a ratio of 5:22 of Alkylbenzene Sulfonate to Sodium Bicarbonate and a ratio of 5:40 of Alkylbenzene Sulfonate to citric acid and
Boric Acid having a ratio of 3:22 of Boric Acid to Sodium Bicarbonate and a ratio of 3:40 of Boric Acid to citric acid.
A composition that provides nutrition enhancing assistance comprising:
Sodium Bicarbonate
Citric Acid
Sodium Lauryl Sulfonate
Polyethylene Glycol
Alkylbenzene Sulfonate
Boric Acid and
an amount within 5% of the value by weight as described by percentage weights: Sodium Bicarbonate 22%, Citric Acid 40%, Sodium Lauryl Sulfonate 20%, Polyethylene Glycol 10%, Alkylbenzene Sulfonate 5%, Boric Acid 3%.
A composition-that provides nutrition enhancing assistance comprising:
Sodium Bicarbonate
Citric Acid
Sodium Lauryl Sulfonate
Polyethylene Glycol
Alkylbenzene Sulfonate
Boric Acid and
an amount within 10% of the value by weight as described by percentage weights: Sodium Bicarbonate 22%, Citric Acid 40%, Sodium Lauryl Sulfonate 20%, Polyethylene Glycol 10%, Alkylbenzene Sulfonate 5%, Boric Acid 3%.
A composition-that provides nutrition enhancing assistance comprising:
Sodium Bicarbonate
Citric Acid
Sodium Lauryl Sulfonate
Polyethylene Glycol
Alkylbenzene Sulfonate
Boric Acid and
an amount within 20% of the value by weight of the compounds as described by percentage weights: Sodium Bicarbonate 22%, Citric Acid 40%, Sodium Lauryl Sulfonate 20%, Polyethylene Glycol 10%, Alkylbenzene Sulfonate 5%, Boric Acid 3%.

In another aspect, wherein the composition is dissolved in a container of water. These and other aspects, features, and advantages of the present invention will become more readily apparent from the attached drawings and the detailed description of the preferred embodiments, which follow.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in the figures if any. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In the context of this disclosure, a number of terms are utilized that are described as follows. The term 'about' means within 20%, preferably within 10% and more preferably within 5% of a given value or range.

General

The novel composition of this invention is a solution with the ingredients dissolved in water or a composition of the combined ingredients in powder or tablet form composed essentially of several components, in particular, Sodium Bicarbonate, Citric Acid, Sodium Lauryl Sulfonate, Polyethylene Glycol, Alkylbenzene Sulfonate and Boric Acid in appropriate proportions for the task. The novel composition can be appropriately water diluted and thereafter applied to the affected trees or plants. In this manner, the application of the mixture substantially reduces, mitigates or even stops the damage caused by some fungal and bacterial diseases, some insects and various nutritional deficits.

First Embodiment

In a preferred embodiment the composition includes essentially all of the above described components in a stable substantially soluble form that has an appreciably long shelf life. The composition is first composed in dry powder form by weight on a percentage by weight basis as follows:

Sodium Bicarbonate 22%
Citric Acid 40%
Sodium Lauryl Sulfonate 20%
Polyethylene Glycol 10%
Alkylbenzene Sulfonate 5%
Boric Acid 3%

The composition thus formed in powder form can be combined with water to make a sprayable solution that has the cited dry percentage based components.

Typically, the composition us made into tablet form with a binding agent or kept in powder form then mixed with water. Next, it is combined with water in a suitable trough or container diluted as one or more tablets per quantity of water. This solution is a safe, non-toxic combination that will not harm the environment.

In order to use it effectively against the diseases that afflict any trees or plants the following procedure should be utilized. The liquid solution is placed in an appropriate spritzer bottle or in a large container such as are used with electromechanical pumps. Then the entire plant or tree is covered including all foliage, limbs and trunks. Finally, the treatment of the tree or plant at least twice a week at first is recommended tapering off to monthly applications.

Second Alternative Embodiment

A second alternative embodiment of the composition described previously includes the same components, however, the components of the composition have different ranges based on the predefined term 'ABOUT'; the composition is first composed in dry powder form by weight on a percentage by weight basis as follows:

Sodium Bicarbonate 'about' 22%
Citric Acid 'about' 40%
Sodium Lauryl Sulfonate 'about' 20%
Polyethylene Glycol 'about' 10%
Alkylbenzene Sulfonate 'about' 5%
Boric Acid 'about' 3%

However, in this embodiment, the components have a percentage basis 'ABOUT' that refers to the flexibility of the amount of each component in the composition as defined previously above. The composition thus formed in powder form can be combined with water to make a sprayable solution that has the cited dry percentage based components.

Typically, the composition us made into tablet form with a binding agent or kept in powder form then mixed with water. Next it is combined with water in a suitable trough or container diluted as one or more tablets per quantity of water. This solution is a safe, non-toxic combination that will not harm the environment.

In order to use it effectively against the diseases that afflict any trees or plants the following procedure should be utilized. The liquid solution is placed in an appropriate spritzer bottle or in a large container such as are used with electromechanical pumps. Then the entire plant or tree is covered including all foliage, limbs and trunks. Finally, the treatment of the tree or plant at least twice a week at first is recommended tapering off to monthly applications.

Third Alternative Embodiment

A third alternative embodiment of the composition described previously includes the same components having different component ranges. However, in this embodiment, the components have a percentage basis and ranges that refers to the flexibility of the amount of each component in the composition. The composition is first composed in dry powder form by weight on a percentage by weight basis as follows:

> Sodium Bicarbonate .05-65%
> Citric Acid .05-70%
> Sodium Lauryl Sulfonate .05-60%
> Polyethylene Glycol .05-30%
> Alkylbenzene Sulfonate .05-35%
> Boric Acid .05-30%

The composition thus formed in powder form can be combined with water to make a sprayable solution that has the cited dry percentage based components.

Typically, the composition us made into tablet form with a binding agent or kept in powder form then mixed with water. Next it is combined with water in a suitable trough or container diluted as one or more tablets per quantity of water. This solution is a safe, non-toxic combination that will not harm the environment.

In order to use it effectively against the diseases that afflict any trees or plants the following procedure should be utilized. The liquid solution is placed in an appropriate spritzer bottle or in a large container such as are used with electromechanical pumps. Then the entire plant or tree is covered including all foliage, limbs and trunks. Finally, the treatment of the tree or plant at least twice a week at first is recommended tapering off to monthly applications.

The three embodiments herein described can be used in any topical application whether foliar or soil based.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A composition that provides plant nutritional assistance comprising:
   Sodium Bicarbonate and
   Citric Acid having a ratio of 40:22 citric acid to sodium bicarbonate.

2. The composition of claim 1 further comprising:
   Sodium Lauryl Sulfonate having a ratio of 20:22 of Sodium Lauryl Sulfonate to Sodium Bicarbonate and a ratio of 20:40 of Sodium Lauryl Sulfonate to citric acid.

3. The composition of claim 1 further comprising:
   Polyethylene Glycol having a ratio of 10:22 of Polyethylene Glycol to Sodium Bicarbonate and a ratio of 10:40 of Polyethylene Glycol to citric acid.

4. The composition of claim 1 further comprising:
   Alkylbenzene Sulfonate having a ratio of 5:22 of Alkylbenzene Sulfonate to Sodium Bicarbonate and a ratio of 5:40 of Alkylbenzene Sulfonate to citric acid.

5. The composition of claim 1 further comprising:
   Boric Acid having a ratio of 3:22 of Boric Acid to Sodium Bicarbonate and a ratio of 3:40 of-Boric Acid to citric acid.

6. The composition of claim 1 further comprising:
   Sodium Lauryl Sulfonate having a ratio of 20:22 of Sodium Lauryl Sulfonate to Sodium Bicarbonate and a ratio of 20:40 of Sodium Lauryl Sulfonate to citric acid and
   Polyethylene Glycol having a ratio of 10:22 of Polyethylene Glycol to Sodium Bicarbonate and a ratio of 10:40 of Polyethylene Glycol to citric acid.

7. The composition of claim 1, further comprising:
   Alkylbenzene Sulfonate having a ratio of 5:22 of Alkylbenzene Sulfonate to Sodium Bicarbonate and a ratio of 5:40 of Alkylbenzene Sulfonate to citric acid and
   Boric Acid having a ratio of 3:22 of Boric Acid to Sodium Bicarbonate and a ratio of 3:40 of-Boric Acid to citric acid.

8. The composition of claim 1, further comprising:
   Sodium Lauryl Sulfonate having a ratio of 20:22 of Sodium Lauryl Sulfonate to Sodium Bicarbonate and a ratio of 20:40 of Sodium Lauryl Sulfonate to citric acid
   Polyethylene Glycol having a ratio of 10:22 of Polyethylene Glycol to Sodium Bicarbonate and a ratio of 10:40 of Polyethylene Glycol to citric acid
   Alkylbenzene Sulfonate having a ratio of 5:22 of Alkylbenzene Sulfonate to Sodium Bicarbonate and a ratio of 5:40 of Alkylbenzene Sulfonate to citric acid and
   Boric Acid having a ratio of 3:22 of Boric Acid to Sodium Bicarbonate and a ratio of 3:40 of Boric Acid to citric acid.

9. A composition that provides plant nutrition enhancing assistance comprising:
   'about' 22% by weight of Sodium Bicarbonate
   'about' 40% by weight of Citric Acid
   'about' 20% by weight of Sodium Lauryl Sulfonate
   'about' 10% by weight of Polyethylene Glycol
   'about' 5% by weight of Alkylbenzene Sulfonate
   'about' 3% by weight of Boric Acid 'about, wherein the 'about' is an amount within 5% of the value by weight of each ingredient thereof.

10. The composition according to 9, wherein the 'about' is an amount within 10% of the value by weight of each ingredient thereof.

11. The composition according to 9, wherein the 'about' is an amount within 20% of the value by weight of each ingredient thereof.

\* \* \* \* \*